US009433554B2

(12) United States Patent
Freeman

(10) Patent No.: US 9,433,554 B2
(45) Date of Patent: Sep. 6, 2016

(54) INTEGRATED RESUSCITATION

(71) Applicant: Zoll Medical Corporation, Chelmsford, MA (US)

(72) Inventor: Gary A. Freeman, Newton Center, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/816,393

(22) Filed: Aug. 3, 2015

(65) Prior Publication Data

US 2015/0352000 A1 Dec. 10, 2015

Related U.S. Application Data

(63) Continuation of application No. 11/942,132, filed on Nov. 19, 2007, now abandoned, which is a continuation of application No. 10/804,312, filed on Mar. 18, 2004, now Pat. No. 7,310,553, which is a (Continued)

(51) Int. Cl.
*A61N 1/39* (2006.01)
*A61H 31/00* (2006.01)
(Continued)

(52) U.S. Cl.
CPC .......... *A61H 31/004* (2013.01); *A61H 31/005* (2013.01); *A61H 31/007* (2013.01); *A61N 1/046* (2013.01); *A61N 1/0492* (2013.01); *A61N 1/39* (2013.01); *A61N 1/3987* (2013.01); *A61N 1/3993* (2013.01); *A61H 2031/002* (2013.01);
(Continued)

(58) Field of Classification Search
USPC ........................................... 607/3, 6; 600/16
See application file for complete search history.

(56) References Cited

U.S. PATENT DOCUMENTS 3,513,850 A 5/1970 Weber
3,865,101 A 2/1975 Saper et al.
(Continued)

FOREIGN PATENT DOCUMENTS

GB 2314648 A 1/1998
WO 9610984 A1 4/1996
(Continued)

OTHER PUBLICATIONS

Abella et al.; Circulation; 2005; 111:428-434.
(Continued)

*Primary Examiner* — Carl H Layno
*Assistant Examiner* — Jon Eric C Morales
(74) *Attorney, Agent, or Firm* — The Webb Law Firm

(57) ABSTRACT

An integrated resuscitation system for use by a rescuer to resuscitate a patient is provided, including: a defibrillation and CPR resuscitation assembly including: a first high-voltage defibrillation electrode; a second high-voltage defibrillation electrode; a compression-sensing element mechanically connected with the first and second electrodes, the compression-sensing element comprising an accelerometer and associated circuitry; and a resuscitation control unit including an internal charge storage capacitor, a microprocessor and associated circuitry configured to be electrically connected to the first and second electrodes and the compression-sensing element and configured to analyze signals generated from the compression-sensing element and at least one of the first electrode and the second electrode to provide resuscitation prompts to the rescuer, wherein the prompts are based at least in part on use of the compression-sensing element by the rescuer.

26 Claims, 12 Drawing Sheets

Related U.S. Application Data continuation of application No. 09/794,320, filed on Feb. 27, 2001, now abandoned, which is a continuation-in-part of application No. PCT/US01/03781, filed on Feb. 5, 2001, now abandoned, which is a continuation-in-part of application No. 09/498,306, filed on Feb. 4, 2000, now abandoned.

(51) Int. Cl.
  *A61N 1/04* (2006.01)
  *A61N 1/08* (2006.01)

(52) U.S. Cl.
  CPC ............. *A61H 2201/5007* (2013.01); *A61H 2201/5043* (2013.01); *A61H 2201/5048* (2013.01); *A61H 2201/5061* (2013.01); *A61H 2201/5084* (2013.01); *A61H 2230/207* (2013.01); *A61N 1/08* (2013.01)

(56) References Cited

U.S. PATENT DOCUMENTS

| | | |
|---|---|---|
| 4,019,501 A | 4/1977 | Harris |
| 4,077,400 A | 3/1978 | Harrigan |
| 4,088,138 A | 5/1978 | Diack et al. |
| 4,095,590 A | 6/1978 | Harrigan |
| 4,193,064 A | 3/1980 | Snyder |
| 4,198,963 A | 4/1980 | Barkalow et al. |
| 4,198,964 A | 4/1980 | Honneffer |
| RE30,372 E | 8/1980 | Mirowski et al. |
| 4,273,114 A | 6/1981 | Barkalow et al. |
| 4,326,507 A | 4/1982 | Barkalow |
| 4,491,423 A | 1/1985 | Cohen |
| 4,588,383 A | 5/1986 | Parker et al. |
| 4,610,254 A | 9/1986 | Morgan et al. |
| 4,619,265 A | 10/1986 | Morgan et al. |
| 4,757,821 A | 7/1988 | Snyder |
| 4,797,104 A | 1/1989 | Laerdal et al. |
| 4,863,385 A | 9/1989 | Pierce |
| 4,928,674 A | 5/1990 | Halperin et al. |
| 4,932,879 A | 6/1990 | Ingenito et al. |
| 5,081,993 A | 1/1992 | Kitney et al. |
| 5,193,537 A | 3/1993 | Freeman |
| 5,241,302 A | 8/1993 | Thong |
| 5,247,945 A | 9/1993 | Heinze et al. |
| 5,285,792 A | 2/1994 | Sjoquist et al. |
| 5,330,526 A | 7/1994 | Fincke et al. |
| 5,348,008 A | 9/1994 | Bornn et al. |
| RE34,800 E | 11/1994 | Hutchins |
| 5,391,187 A | 2/1995 | Freeman |
| 5,409,010 A | 4/1995 | Beach et al. |
| 5,454,779 A | 10/1995 | Lurie et al. |
| 5,466,244 A | 11/1995 | Morgan |
| 5,472,453 A | 12/1995 | Alt |
| 5,474,574 A | 12/1995 | Payne et al. |
| 5,496,257 A | 3/1996 | Kelly |
| 5,507,778 A | 4/1996 | Freeman |
| 5,511,553 A | 4/1996 | Segalowitz |
| 5,514,079 A | 5/1996 | Dillon |
| 5,533,958 A | 7/1996 | Wilk |
| 5,562,710 A | 10/1996 | Olsen et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,645,522 A | 7/1997 | Lurie et al. |
| 5,645,571 A | 7/1997 | Olson et al. |
| 5,662,690 A | 9/1997 | Cole et al. |
| 5,700,281 A | 12/1997 | Brewer et al. |
| 5,735,879 A | 4/1998 | Gliner et al. |
| 5,787,880 A | 8/1998 | Swanson et al. |
| 5,792,190 A | 8/1998 | Olson et al. |
| 5,853,292 A | 12/1998 | Eggert et al. |
| 5,913,685 A | 6/1999 | Hutchins |
| 5,957,856 A | 9/1999 | Weil et al. |
| 5,993,398 A | 11/1999 | Alperin |
| 6,021,349 A | 2/2000 | Arand et al. |
| 6,120,442 A | 9/2000 | Hickey |
| 6,125,299 A | 9/2000 | Groenke et al. |
| 6,155,257 A | 12/2000 | Lurie et al. |
| 6,178,357 B1 | 1/2001 | Gliner et al. |
| 6,193,519 B1 | 2/2001 | Eggert et al. |
| 6,220,866 B1 | 4/2001 | Amend et al. |
| 6,224,562 B1 | 5/2001 | Lurie et al. |
| 6,238,349 B1 | 5/2001 | Hickey |
| 6,306,107 B1 | 10/2001 | Myklebust et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,371,765 B1 | 4/2002 | Wall et al. |
| 6,390,996 B1 * | 5/2002 | Halperin et al. ............. 601/41 |
| 6,428,323 B1 | 8/2002 | Pugh |
| 6,443,735 B1 | 9/2002 | Eggert et al. |
| 6,503,087 B1 | 1/2003 | Eggert et al. |
| 6,572,547 B2 | 6/2003 | Miller et al. |
| 6,575,914 B2 | 6/2003 | Rock et al. |
| 6,752,771 B2 | 6/2004 | Rothman et al. |
| 6,827,695 B2 | 12/2004 | Palazzolo et al. |
| 6,961,612 B2 | 11/2005 | Elghazzawi et al. |
| 7,010,344 B2 | 3/2006 | Burnes et al. |
| 7,072,712 B2 | 7/2006 | Kroll et al. |
| 7,118,542 B2 | 10/2006 | Palazzolo et al. |
| 7,122,007 B2 | 10/2006 | Querfurth |
| 7,164,945 B2 | 1/2007 | Hamilton et al. |
| 7,190,999 B2 | 3/2007 | Geheb et al. |
| 7,220,235 B2 | 5/2007 | Geheb et al. |
| 7,454,244 B2 | 11/2008 | Kassab et al. |
| 7,761,139 B2 | 7/2010 | Tearney et al. |
| 7,822,470 B2 | 10/2010 | Osypka et al. |
| 7,837,669 B2 | 11/2010 | Dann et al. |
| 7,846,138 B2 | 12/2010 | Dann et al. |
| 8,012,135 B2 | 9/2011 | Dann et al. |
| 2001/0018562 A1 | 8/2001 | Sherman et al. |
| 2002/0024888 A1 | 2/2002 | Schreiber |
| 2002/0026131 A1 | 2/2002 | Halperin |
| 2002/0026229 A1 | 2/2002 | Weil et al. |
| 2002/0055694 A1 | 5/2002 | Halperin et al. |
| 2002/0133197 A1 | 9/2002 | Snyder et al. |
| 2002/0165471 A1 | 11/2002 | Halperin et al. |
| 2002/0193711 A1 | 12/2002 | Halperin et al. |
| 2003/0014055 A1 | 1/2003 | Svadovskiy |
| 2003/0055460 A1 | 3/2003 | Owen et al. |
| 2003/0083699 A1 | 5/2003 | Hamilton et al. |
| 2003/0158593 A1 | 8/2003 | Heilman et al. |
| 2003/0192547 A1 | 10/2003 | Lurie et al. |
| 2004/0039313 A1 | 2/2004 | Sherman et al. |
| 2004/0039419 A1 | 2/2004 | Stickney et al. |
| 2004/0044374 A1 | 3/2004 | Weinberg et al. |
| 2004/0049118 A1 | 3/2004 | Ideker et al. |
| 2004/0058305 A1 | 3/2004 | Lurie et al. |
| 2004/0162510 A1 | 8/2004 | Jayne et al. |
| 2004/0162585 A1 | 8/2004 | Elghazzawi et al. |
| 2004/0162586 A1 | 8/2004 | Covey et al. |
| 2004/0162587 A1 | 8/2004 | Hampton et al. |
| 2004/0186525 A1 | 9/2004 | Burnes et al. |
| 2004/0210171 A1 | 10/2004 | Palazzolo et al. |
| 2004/0214148 A1 | 10/2004 | Salvino et al. |
| 2004/0230140 A1 | 11/2004 | Steen |
| 2004/0267325 A1 | 12/2004 | Geheb et al. |
| 2005/0119706 A1 | 6/2005 | Ideker et al. |
| 2005/0137628 A1 | 6/2005 | Young et al. |
| 2005/0209503 A1 | 9/2005 | Elliott |
| 2005/0256415 A1 | 11/2005 | Tan et al. |
| 2005/0261742 A1 | 11/2005 | Nova et al. |
| 2006/0009809 A1 | 1/2006 | Marcovecchio et al. |
| 2006/0036292 A1 | 2/2006 | Smith et al. |
| 2006/0041278 A1 | 2/2006 | Cohen et al. |
| 2006/0089574 A1 | 4/2006 | Paradis |
| 2006/0116724 A1 | 6/2006 | Snyder |
| 2006/0173500 A1 | 8/2006 | Walker et al. |
| 2006/0174501 A1 | 8/2006 | Harrill |
| 2006/0224053 A1 | 10/2006 | Black et al. |

(56) References Cited

U.S. PATENT DOCUMENTS

| | | |
|---|---|---|
| 2006/0257377 A1 | 11/2006 | Atala et al. |
| 2007/0054254 A1 | 3/2007 | Cook et al. |
| 2008/0176199 A1 | 7/2008 | Stickney et al. |

FOREIGN PATENT DOCUMENTS

| | | |
|---|---|---|
| WO | 9830282 A1 | 7/1998 |
| WO | 9839061 A2 | 9/1998 |
| WO | 9924114 A1 | 5/1999 |
| WO | 9925306 A1 | 5/1999 |
| WO | 9963926 A2 | 12/1999 |
| WO | 9965560 A2 | 12/1999 |
| WO | 0156652 A1 | 8/2001 |
| WO | 0166182 A1 | 9/2001 |
| WO | 0215836 A2 | 2/2002 |
| WO | 02072197 A2 | 9/2002 |
| WO | 03009895 A1 | 2/2003 |
| WO | 2004037154 A2 | 5/2004 |
| WO | 2004054656 A1 | 7/2004 |
| WO | 2004073493 A2 | 9/2004 |
| WO | 2004078259 A1 | 9/2004 |
| WO | 2005021089 A1 | 3/2005 |

OTHER PUBLICATIONS

Crit. Care Med; 2000; vol. 28, No. 11 (Suppl.).

Eftestol et al.: "Predicting Outcome of defibrillation by Spectral Characterization and Nonparametric Classification of Ventricular Figrillation in Patients with Out-of-Hospital Cardiac Arrest"; Circulation, 2000.

Pinsky; Journal of Applied Physiology; Feb. 1986; pp. 604-612; vol. 60(2).

Sato et al.; Critical Care Medicine; May 1997; pp. 733-736; vol. 25(5).

Yu et al.: "Adverse Outcomes of Interrupted Precordial Compression During Automated Defibrillation"; Circulation; 2002.

AAse et al.: "Compression Depth Estimation for CPR Quality Assessment Using DSP on Accelerometer Signals"; IEEE Transactions on Biomedical Engineering; Mar. 2002; vol. 49, No. 3.

American Red Cross—Adult CPR/AED Training—Workplace Programs; http://www.redcross.org/hss/opraed html/ printed from Internet May 14, 1999.

Force Sensing Resistors—An Overview of the Technology, FSR Integration Guide & Evaluation Parts Catalog with Suggested Electrical Interfaces (no date).

Gruben et al.; "System for Mechanical Measurements During Cardiopulmonary Resuscitation in Humans"; IEEE Transactions for Biomedical Engineering, Feb. 1990, vol. 37, No. 2.

"Heartstream—The Background Behind Our Technology"; http://www.heartstream.com/techbk.htm, pringed from Internat Jun. 25, 1999.

Flewelling Nellcor Incorporated, Noninvasive Optical Monitoring; Chap. 88, pp. 1346-1353, CRC Press, Inc. 1995.

\* cited by examiner

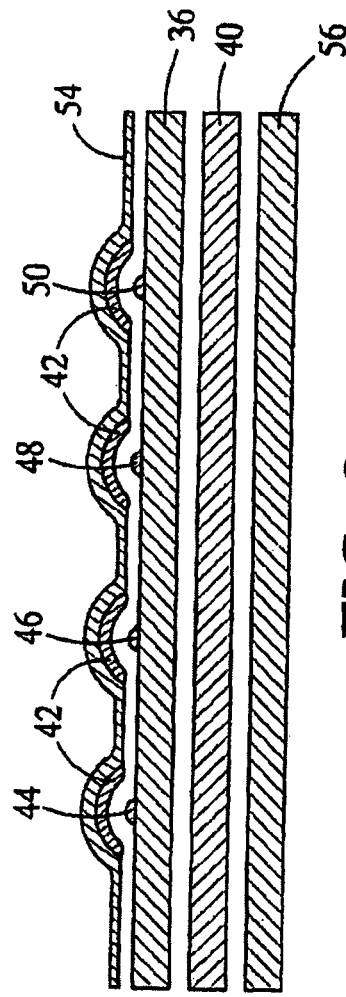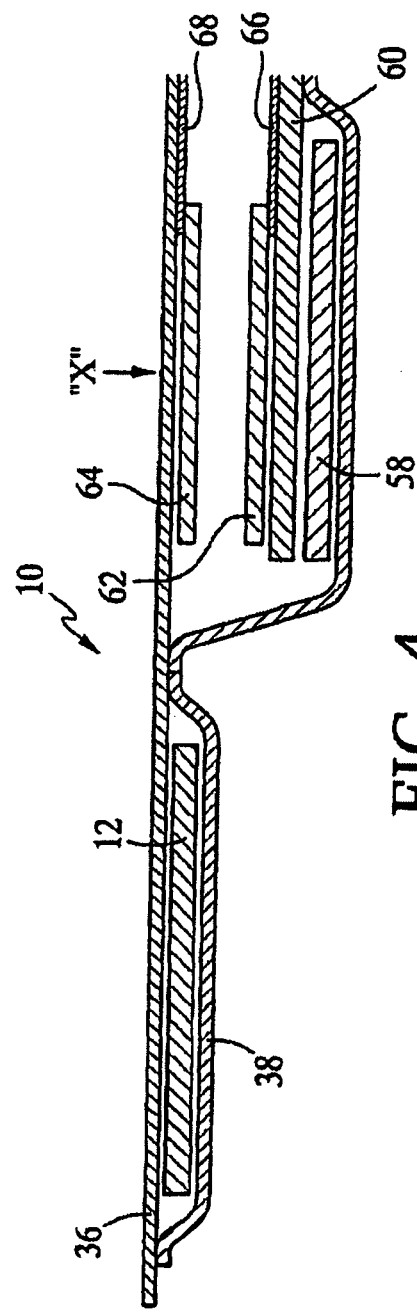

INTEGRATED RESUSCITATION

CROSS REFERENCE TO RELATED APPLICATIONS

This application is a continuation of and claims priority to U.S. patent application Ser. No. 11/942,132, filed on Nov. 19, 2007, which is a continuation of and claims priority to U.S. patent application Ser. No. 10/804,312, filed on Mar. 18, 2004 (U.S. Pat. No. 7,310,553), which is a continuation of and claims priority to U.S. patent application Ser. No. 09/794,320, filed on Feb. 27, 2001 (now abandoned), which is a continuation-in-part of and claims priority to PCT Application No. PCT/US01/03781, filed on Feb. 5, 2001, which is a continuation-in-part and claims priority to U.S. patent application Ser. No. 09/498,306, filed on Feb. 4, 2000 (now abandoned), each of which is incorporated by reference herein in their entireties.

BACKGROUND OF THE INVENTION

1. Field of the Invention

This invention relates to integrated resuscitation systems incorporating defibrillation and cardio-pulmonary resuscitation (CPR) prompts.

2. Description of Related Art

Resuscitation can generally include clearing a patient's airway, assisting the patient's breathing, chest compressions, and defibrillation.

The American Heart Association's Basic Life Support for Health Care Providers textbook provides a flow chart at page 4-14 of Chapter 4 that lists the steps of airway clearing, breathing, and circulation (known as A, B, and C), for situations in which there is no defibrillator readily accessible to the rescuer.

Defibrillation (sometimes known as step D) can be performed with the use of an automatic external defibrillator (AED). Most automatic external defibrillators are actually semi-automatic external defibrillators (SAED), which require a clinician to press a start button, after which the defibrillator analyzes the patient's condition and provides a shock to the patient if the electrical rhythm is shockable and waits for user intervention before any subsequent shock. Fully automatic external defibrillators, on the other hand, do not wait for user intervention before applying subsequent shocks. As used below, automatic external defibrillators (AED) include semi-automatic external defibrillators (SAED).

Both types of defibrillators typically provide an oral stand clear warning before the application of each shock, and then the clinician is expected to stand clear of the patient and may be required to press a button indicating that the clinician is standing clear of the patient. The controls for automatic external defibrillators are typically located on a resuscitation control box.

AEDs arc used typically by trained providers such as physicians, nurses, fire department personnel, and police officers. There might be one or two people at a given facility that has an AED who have been designated for defibrillation resuscitation before an ambulance service arrives. The availability of on-site AEDs along with rescuers trained to operate them is important because if the patient experiences a delay of more than 4 minutes before receiving a defibrillation shock the patient's chance of survival can drop dramatically. Many large cities and rural areas have low survival rates for defibrillation because the ambulance response time is slow, although many suburbs have higher survival rates because of the faster ambulance response time due to lack of traffic and availability of hospitals and advanced life support.

Trained lay providers are a new group of AED operators, but they rarely have opportunities to defibrillate. For example, spouses of heart attack victims may become lay providers, but these lay providers can be easily intimidated by an AED during a medical emergency. Consequently, such lay providers can be reluctant to purchase AEDs, or might tend to wait for an ambulance to arrive rather than use an available AED, out of concern that the lay provider might do something wrong.

There are many different kinds of heart rhythms, some of which are considered shockable and some of them are not. For example, a normal rhythm is considered non-shockable, and there are also many abnormal non-shockable rhythms. There are also some abnormal non-viable non-shockable, which means that the patient cannot remain alive with the rhythm, but yet applying shocks will not help convert the rhythm.

As an example of a non-shockable rhythm, if a patient experiences asystole, the heart will not be beating and application of shocks will be ineffective. Pacing is recommended for asystole, and there are other things that an advanced life support team can do to assist such patient, such as the use of drugs. The job of the first responder is simply to keep the patient alive, through the use of CPR and possibly defibrillation, until an advanced life support team arrives. Bradycardias, during which the heart beats too slowly, are non-shockable and also possibly non-viable. If the patient is unconscious during bradycardia, it can be helpful to perform chest compressions until pacing becomes available. Electro-mechanical dissociation (EMD), in which there is electrical activity in the heart but it is not making the heart muscle contract, is non-shockable and non-viable, and would require CPR as a first response. Idio-ventricular rhythms, in which the normal electrical activity occurs in the ventricles but not the atria, can also be non-shockable and non-viable (usually, abnormal electrical patterns begin in the atria). Idio-ventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles.

The primary examples of shockable rhythms, for which a first responder should perform defibrillation, include ventricular fibrillation, ventricular tachycardia, and ventricular flutter.

After using a defibrillator to apply one or more shocks to a patient who has a shockable electrical rhythm, the patient may nevertheless remain unconscious, in a shockable or non-shockable rhythm. The rescuer may then resort to chest compressions. As long as the patient remains unconscious, the rescuer can alternate between use of the defibrillator (for analyzing the electrical rhythm and possibly applying a shock) and performing cardio-pulmonary resuscitation (CPR).

CPR generally involves a repeating pattern of five or fifteen chest compressions followed by a pause. CPR is generally ineffective against abnormal rhythms, but it does keep some level of blood flow going to the patient's vital organs until an advanced life support team arrives. It is difficult to perform CPR over an extended period of time. Certain studies have shown that over a course of minutes, rescuers tend to perform chest compressions with less-than-sufficient strength to cause an adequate supply of blood to flow to the brain. CPR prompting devices can assist a rescuer by prompting each chest compression and breath.

PCT Patent Publication No. WO 99/24114, filed by Heartstream, Inc., discloses an external defibrillator having PCR and ACLS (advanced cardiac life support) prompts.

SUMMARY OF THE INVENTION

One aspect of the invention features a resuscitation system comprising at least two defibrillation electrodes configured to be applied to the exterior of the chest of a patient for delivering a defibrillation shock; a source of one or more ECG signals from the patient; a defibrillation circuit for delivering a defibrillation shock to the defibrillation electrodes; a control box that receives and processes the ECG signals to determine whether a defibrillation shock should be delivered or whether CPR should be performed, and that issues instructions to the user either to deliver a defibrillation shock or to perform CPR, wherein the determination of whether CPR should be performed and the instructions to perform CPR can occur at substantially any point during a rescue.

In preferred implementations, one or more of the following features are incorporated. The control box includes a user operable control for initiating delivery of a defibrillation shock, and the instructions to deliver a defibrillation shock include instructions to activate the user operable control. The user operable control is a button configured to be pushed by the user. The determination of whether CPR should be performed and the instructions to perform CPR can occur before a determination to deliver any defibrillation shock. The source of the ECG signals is the defibrillation electrodes. The defibrillation circuit is contained in the control box.

Numerous other features and advantages of the invention will be apparent from the detailed description and the drawings.

BRIEF DESCRIPTION OF THE DRAWING(S)

FIG. 3 is a cross-sectional drawing of the defibrillation electrode pad of FIG. 1 taken along line 3-3.

FIG. 4 is a cross-sectional drawing of the defibrillation pad of FIG. 1 taken along line 4-4.

Figure 7A:
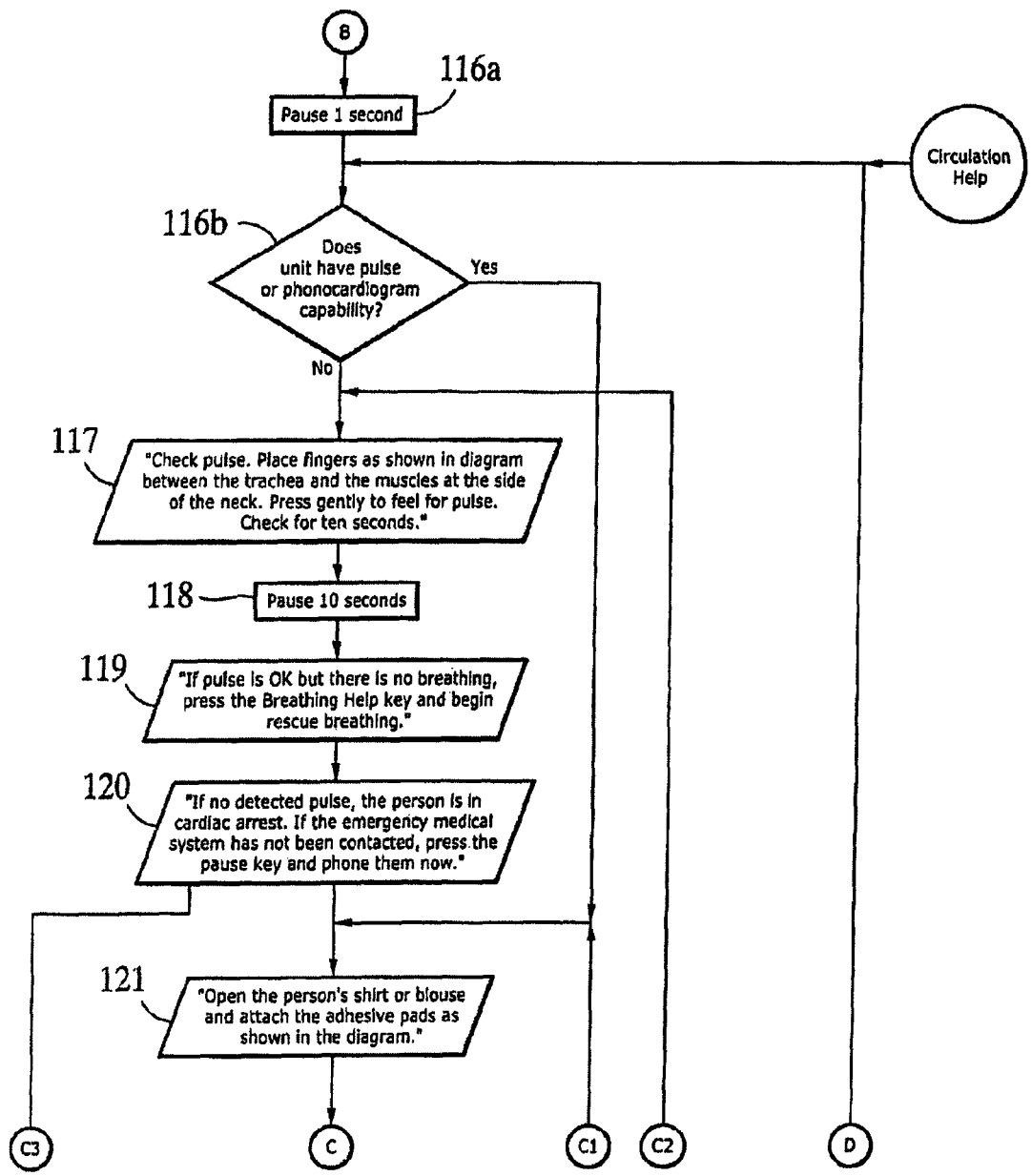
Figure 7B:
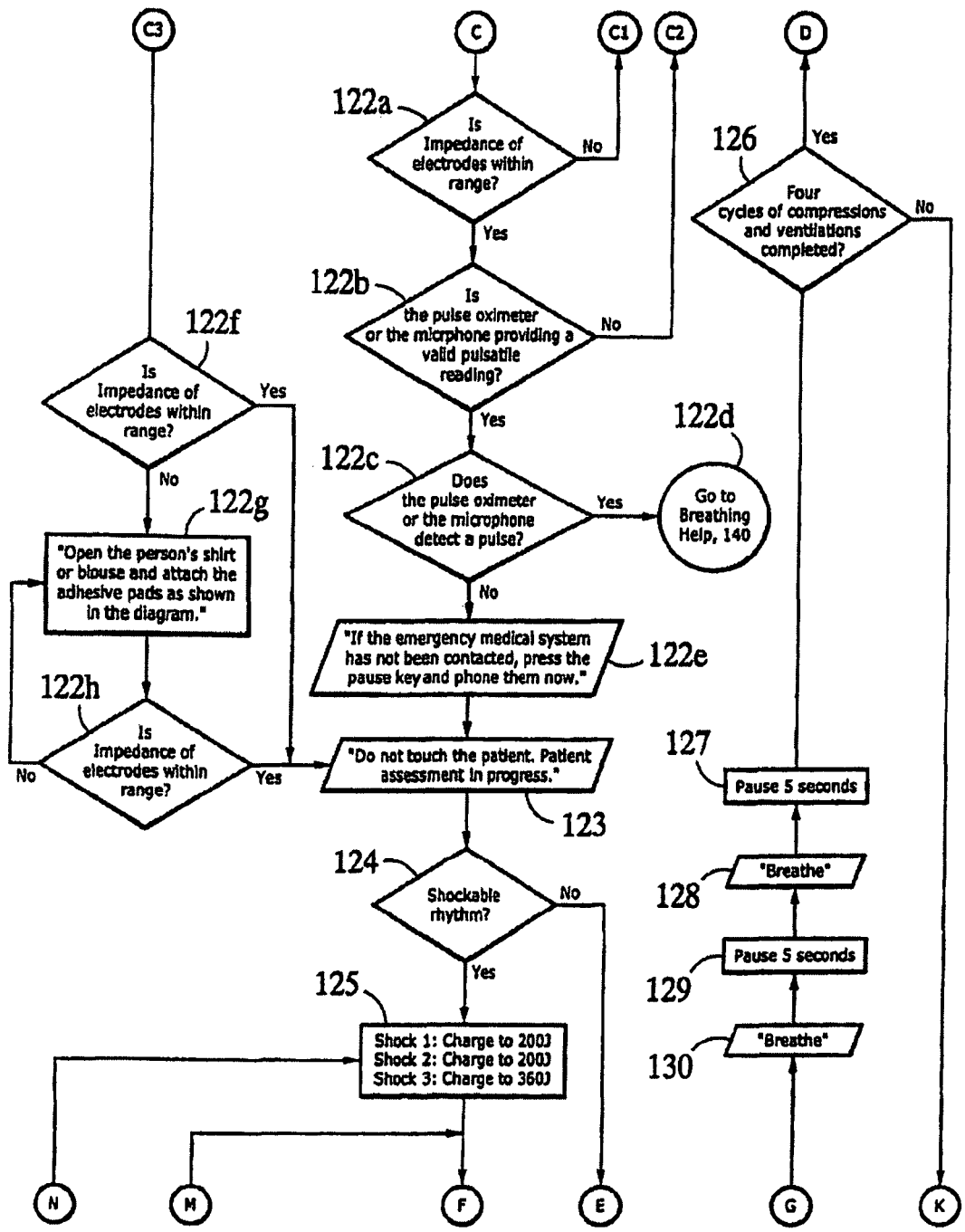
Figure 7C:
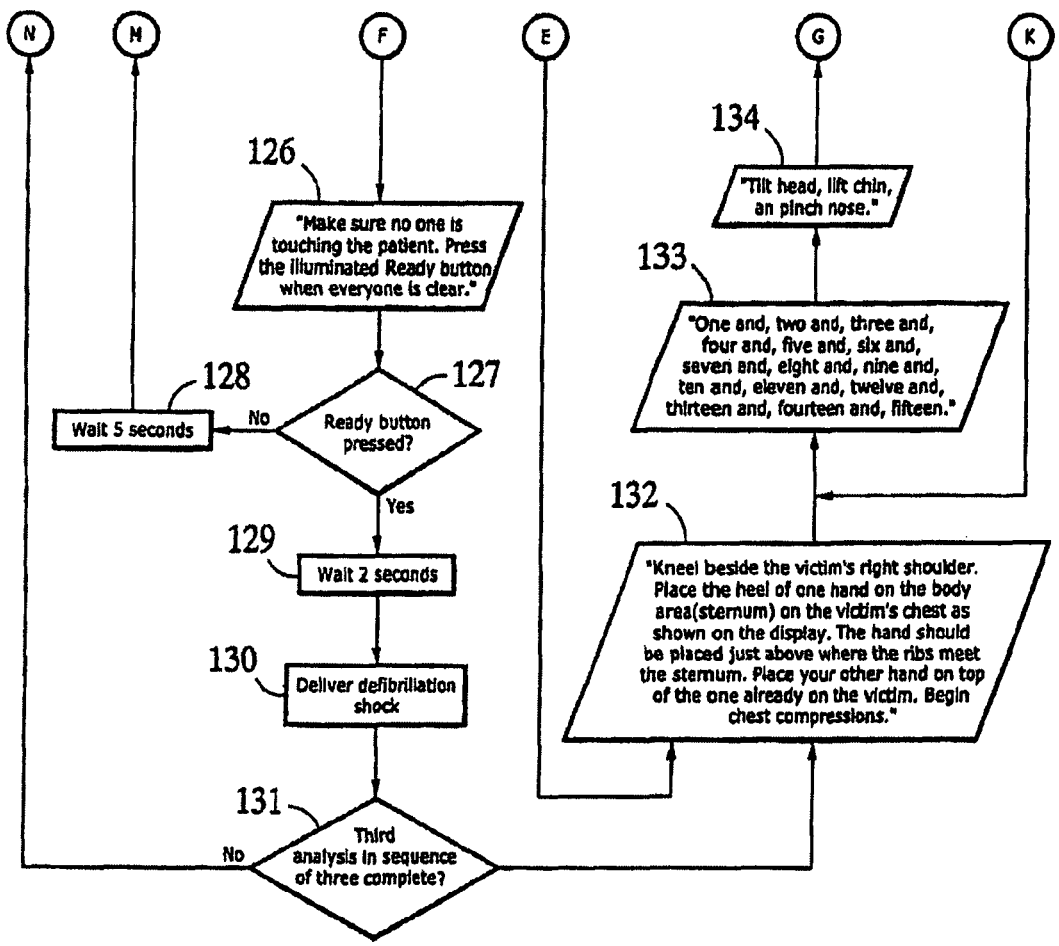

FIGS. 7A, 7B, and 7C are a flowchart illustrating the "circulation help" routine of the resuscitation system.

Figure 8:
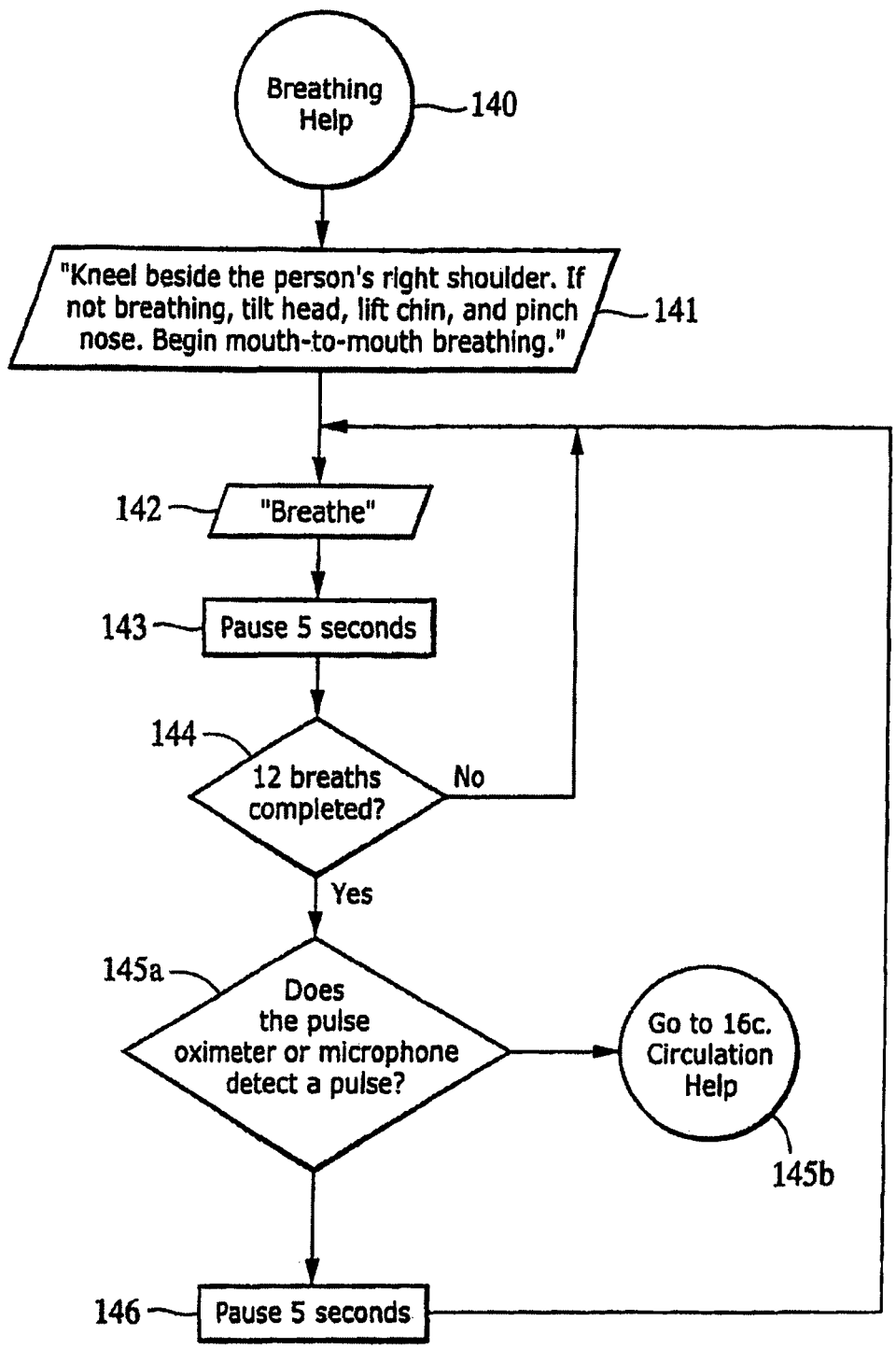

FIG. 8 is a flowchart illustrating the "breathing help" routine of the resuscitation system.

Figure 9A:
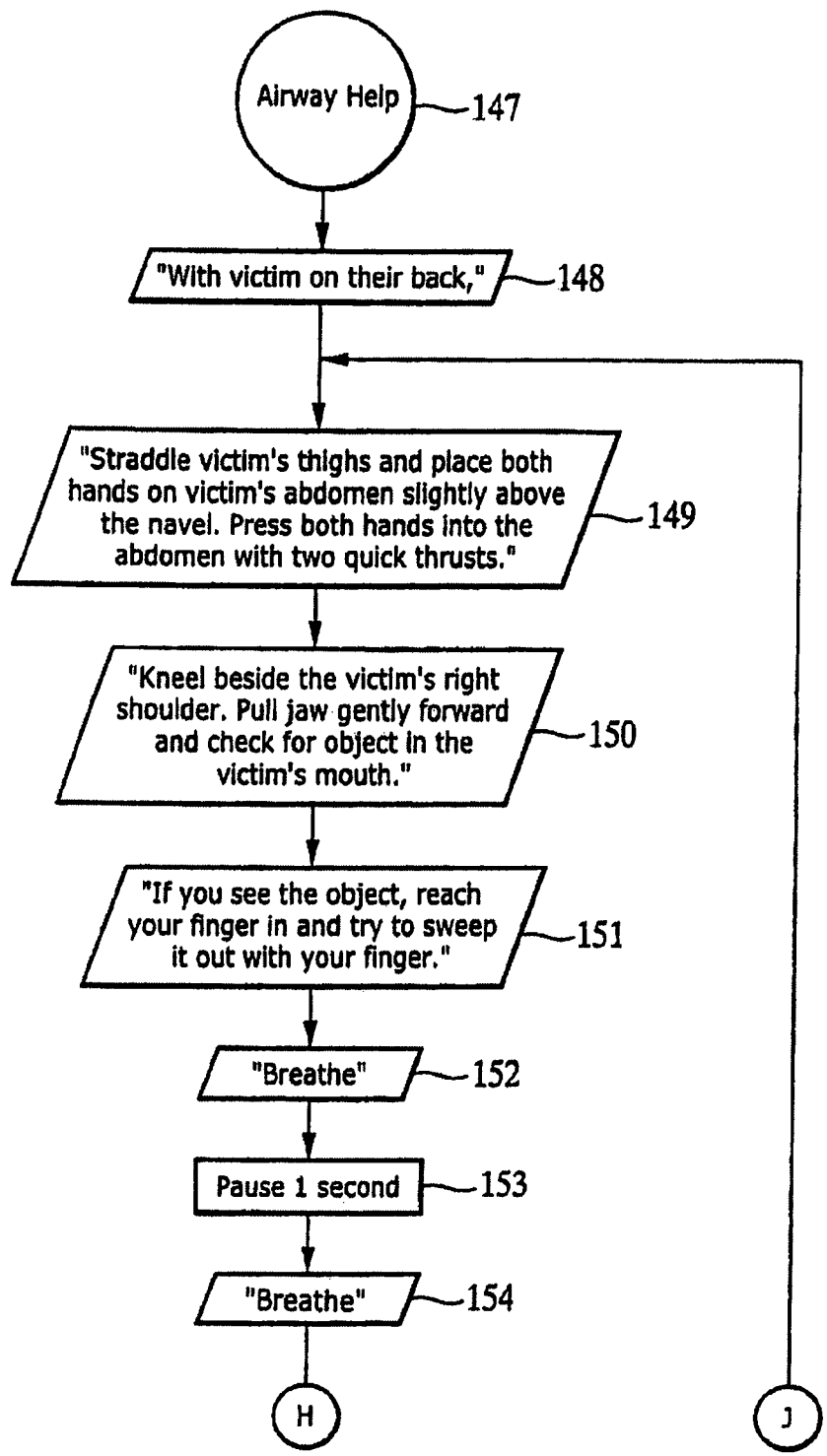
Figure 9B:
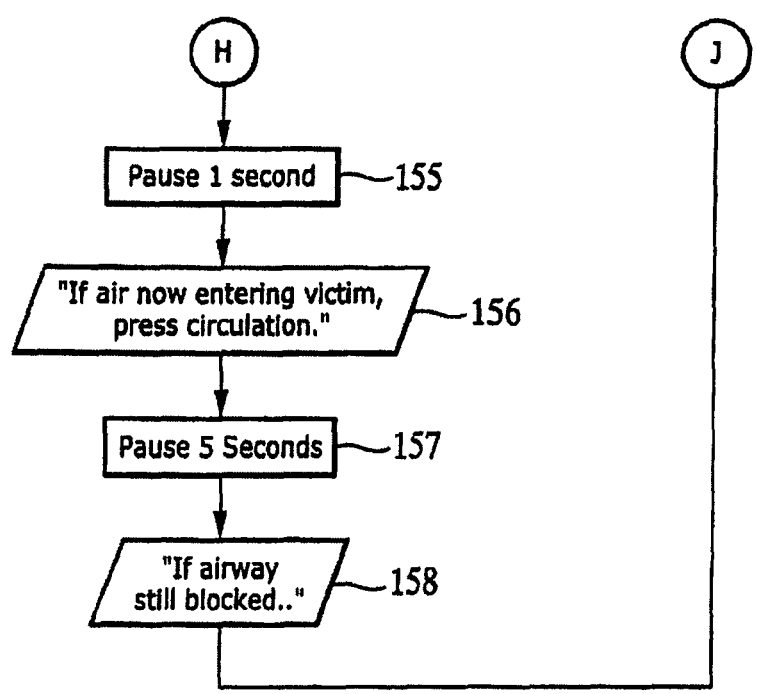

FIGS. 9A and 9B are a flow chart illustrating the "airway help" routine of the resuscitation system.

DESCRIPTION OF THE INVENTION

The defibrillation and CPR assembly according to the invention combines traditional AED (automatic external defibrillation) functions with CPR prompting, and thus transforms a defibrillator into a resuscitation device that combines prompts for clearing a patient's airway, breathing, chest compression, and defibrillation. Thus, the combined defibrillation and CPR assembly combines all of these aspects of resuscitation into a single protocol.

Figure 1:
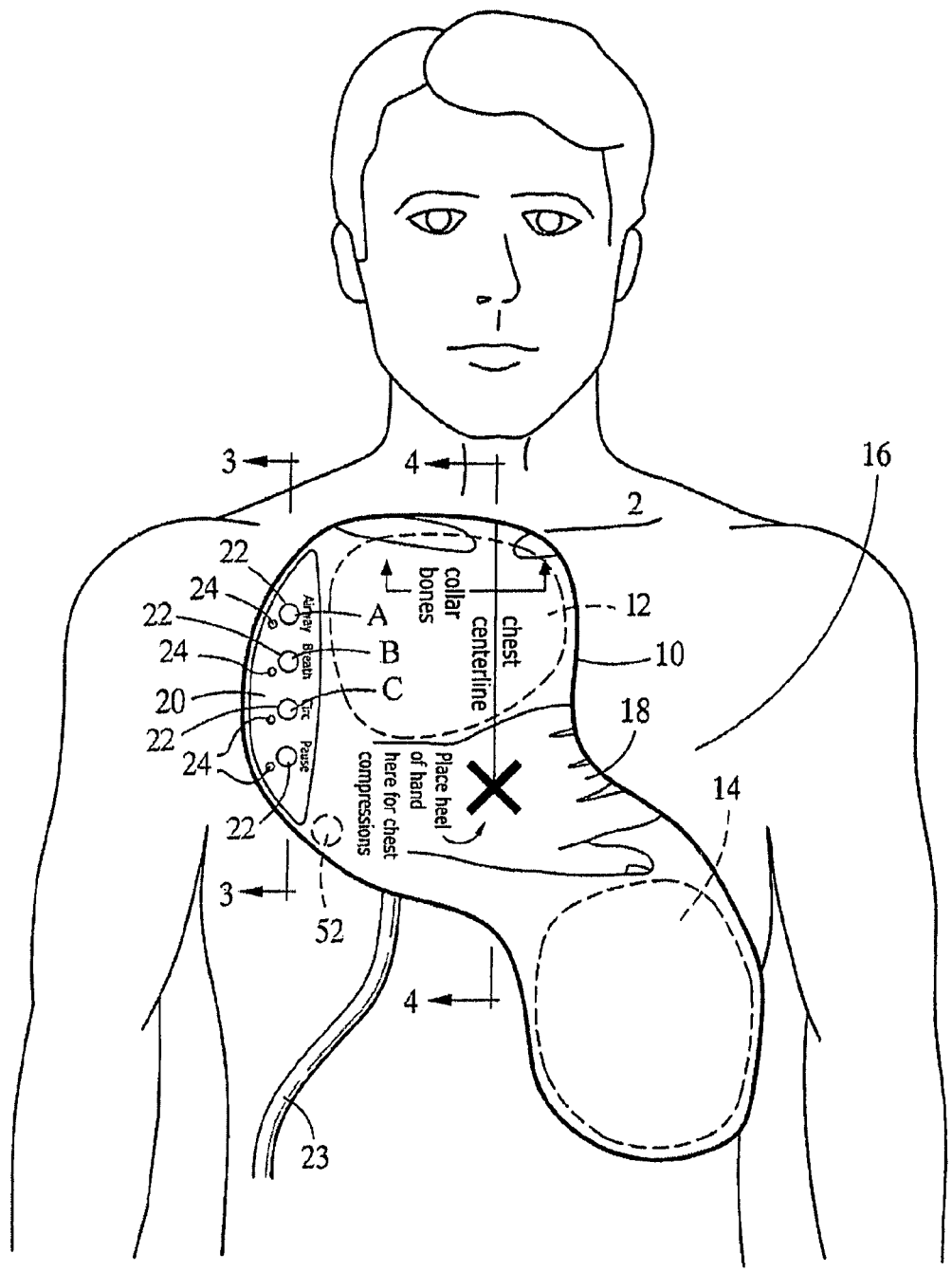
FIG. 1 is a drawing of a defibrillation electrode pad according to the invention, positioned over the chest of a patient.

With reference to FIG. 1, a defibrillation electrode pad 10, which includes high-voltage apex defibrillation electrode 12 and high-voltage sternum defibrillation electrode 14, is placed on the patient's chest 16 and includes a region 18 on which a user may press to perform CPR. Legends on pad 10 indicate proper placement of the pad with respect to the patient's collarbones and the chest centerline and the proper placement of the heel of the rescuer's hand.

A low-profile button panel 20 is provided on the electrode assembly. Button panel 20 has buttons 22, including buttons A (Airway Help), B (Breathing Help), C (Circulation Help) and PAUSE, and may also include adjacent light emitting diodes (LEDs) 24 that indicate which button has been most recently pressed. Button panel 20 is connected by a cable 23 to a remote resuscitation control box 26, shown in FIG. 2.

Button panel 20 provides rigid support underneath buttons A, B, C, and PAUSE against which the switches can be pushed in order to ensure good switch closure while the electrode rests on a patient. Button panel 20 includes components that make electrical contact with silver/silver-chloride electrical circuit components screen-printed on a polyester base of defibrillation electrode pad 10, as is described in detail below.

A pulse detection system based on shining light through the patient's vascular bed, e.g., a pulse oximetry system 52, is incorporated into defibrillation electrode pad 10. Pulse oximetry system 52 includes a red light-emitting diode, a near-infrared light emitting diode, and a photodetector diode (see FIG. 5) incorporated into defibrillation electrode pad 10 in a manner so as to contact the surface of the patient's chest 16. The red and near-infrared light-emitting diodes emit light at two different wavelengths, which is diffusely scattered through the patient's tissue and detected by the photodetector diode. The information obtained from the photodetector diode can be used to determine whether the patient's blood is oxygenated, according to known noninvasive optical monitoring techniques.

In an alternative embodiment, the pulse detection system is a phonocardiogram system for listening to the sound of the victim's heart, rather than a pulse oximetry system. The phonocardiogram system includes a microphone and an amplifier incorporated within the electrode pad. Because a heart sound can be confused with microphone noise, the signal processing that must be performed by the microprocessor inside the control box will be more difficult in connection with a phonocardiogram system than in connection with a pulse oximetry system. Nevertheless, there are programs available that can enable the microprocessor to determine whether an ECG signal is present as opposed to microphone noise.

Pulse oximetry is a well-developed, established technology, but it requires good contact between the light sources and the victim's skin so that light can shine down into the victim's vascular bed. Many victims have lots of chest hair, which can interfere with good contact. It may be desirable for different types of electrode pads to be available at a given location (one having a pulse oximetry system and one having a phonocardiogram system) so that a rescuer can select an appropriate electrode pad depending on the nature of the victim.

In an alternative embodiment, instead of providing a low-profile button panel a button housing can be provided that is affixed to an edge of the defibrillation electrode. The housing may be in the form of a clamshell formed of single molded plastic element having a hinge at an edge of the clamshell around which the plastic bends. The two halves of the clamshell can be snapped together around the electrode assembly.

The resuscitation control box (FIG. 2) includes an internal charge storage capacitor and associated circuitry including a microprocessor, and further includes off/on dial 28, and a "READY" button 30 that the rescuer presses immediately prior to application of a defibrillation shock in order to ensure that the rescuer is not in physical contact with the patient. The microprocessor may be a RISC processor such as a Hitachi SH-3, which can interface well with displays and keyboards, or more generally a processor capable of handling DSP-type (digital signal processing) operations.

The resuscitation control box has printed instructions 32 on its front face listing the basic steps A, B, and C for resuscitating a patient and giving basic instructions for positioning the defibrillation electrode pad on the patient. A speaker orally prompts the user to perform various steps, as is described in detail below.

For example, the resuscitation control box instructs the user, by audible instructions and also through a display 34 on the resuscitation control box, to check the patient's airway and perform mouth-to-mouth resuscitation, and if the patient's airway is still blocked, to press the A (Airway Help) button on the button panel (FIG. 1), upon which the resuscitation control box gives detailed prompts for clearing the patient's airway. If the patient's airway is clear and the patient has a pulse but the patient does not breathe after initial mouth-to-mouth resuscitation, the resuscitation control box instructs the user to press the B (Breathing Help) button, upon which the resuscitation control box gives detailed mouth-to-mouth resuscitation prompts. If, during the detailed mouth-to mouth resuscitation procedure, the rescuer checks the patient's pulse and discovers that the patient has no pulse, the resuscitation control box instructs the user to press the C (Circulation Help) button.

During the circulation procedure, the resuscitation control box receives electrical signals from the defibrillation electrodes and determines whether defibrillation or CPR should be performed. If the resuscitation control box determines that defibrillation is desirable, the resuscitation control box instructs the user to press the "ready" button on the resuscitation control box and to stand clear of the patient. After a short pause, the resuscitation control box causes a defibrillation pulse to be applied between the electrodes. If at any point the resuscitation control box determines, based on the electrical signals received from the electrodes, that CPR is desirable, it will instruct the user to perform CPR.

Thus, the key controls for the system are on the electrodes attached to the patient rather than the resuscitation control box. This is important because it enables the rescuer to remain focused on the patient rather than the control box. The resuscitation control box gets its information directly from the electrodes and the controls on the electrodes.

The resuscitation control box can sense electrical signals from the patient's body during pauses between CPR compressions. Also, as is described below, a compression-sensing element such as an accelerometer or a force-sensing element is provided in the region of the defibrillation electrode pad on which the user presses to perform CPR. The purpose of the compression-sensing or force-sensing element is to allow the resuscitation control box to prompt the user to apply additional compression or force, or to prompt the user to cease CPR if the user is performing CPR at an inappropriate point in time.

Referring to FIG. 4, according to one embodiment of the invention, each electrode 12, 14 (only electrode 12 is shown) of defibrillation electrode pad 10 includes a polymer-based ink containing a silver/silver-chloride suspension, which is screen-printed on a polyester or plastic base 36. The ink is used to carry the defibrillation current. The screen-printing process first involves applying a resist layer to the polyester base 36. The resist layer is basically a loose mesh of nylon or the like, in which the holes have been filled in at some locations in the mesh. Then, the silver/silver-chloride ink is applied as a paste through the resist layer in a squeegee-like manner. The ink squeezes through the screen and becomes a solid layer. The ink may then be cured or dried. The silver/silver-chloride ink provides good conductivity and good monitoring capabilities.

Thus, the ink can be applied as pattern, as opposed to a solid sheet covering the entire polyester base. For example, U.S. Pat. No. 5,330,526 describes an electrode in which the conductive portion has a scalloped or daisy shape that increases the circumference of the conductive portion and reduces burning of the patient. A conductive adhesive gel 38 covers the exposed surface of each electrode.

In addition, electrical circuit components are also screen printed on the base, in the same manner as flat circuit components of membrane-covered, laminated panel controls.

Referring to FIG. 3, a rigid piece 40 of hard plastic, such as PVC or polycarbonate, is laminated beneath substrate 36 and supports buttons A, B, C, and PAUSE. The rigid plastic piece 40 is glued onto substrate 36. Buttons A, B, C, and PAUSE consist of small metal dome snap-action switches that make contact between an upper conductive ink trace 42 and lower conductive ink truces 44, 46, 48, and 50. Buttons A, B, C, and PAUSE serve as controls that can be activated by the user that are physically located either on or immediately adjacent to the electrode assembly itself. Each of buttons A, B, C, and PAUSE may be associated with an adjacent light-emitting diode (LED). For example, LEDs may be glued, using conductive epoxy, onto silver/silver-chloride traces on substrate 36. An embossed polyester laminate layer 54 covers conductive ink trace 42 of buttons A, B, C, and PAUSE, and a foam layer 56 is laminated beneath rigid plastic piece 40.

Referring again to FIG. 4, defibrillation electrode pad 10 includes an extension piece that is placed directly over the location on the patient's body where the rescuer performs chest compressions. This extension piece includes substrate 36, and a semi-rigid plastic supporting member 58 laminated underneath substrate 36 that covers the chest compression area. Semi-rigid supporting member 58 provides somewhat less rigidity than rigid plastic piece 40 provided at the location of buttons A, B, C, and PAUSE (illustrated in FIG. 3).

In embodiments having a force-sensing element, a polyester laminate 60, and a force-sensing resistor having two layers of carbon-plated material 62 and 64, are laminated between polyester substrate 36 and semi-rigid supporting member 58. A suitable construction of the force-sensing resistor is illustrated in the FSR Integration Guide & Evaluation Parts Catalog with Suggested Electrical Interfaces, from Interlink Electronics. The electrical contact between the two carbon-plated layers of material increases with increased pressure, and the layers of force-sensing resistive material can provide a generally linear relationship between resistance and force. Conductive ink traces 66 and 68 provide electrical connections to the two layers of the force-sensing resistor.

During chest compressions, the rescuer's hands are placed over the extension piece, and the force-sensing resistor of the extension piece is used to sense the force and the timing of the chest compressions. The force-sensing resistor provides information to the resuscitation control box so that the resuscitation control box can provide the rescuer with feedback if the rescuer is applying insufficient force. The resuscitation control box also provides coaching as to the rate at which CPR is performed. In certain situations, the resuscitation control box indicates to the rescuer that CPR should be halted because it is being performed at an inappropriate time, such as immediately prior to application of a defibrillation shock when the rescuer's hands should not be touching the patient, in which case the resuscitation control box will also indicate that the rescuer should stay clear of the patient because the patient is going to experience a defibrillation shock.

As is noted above, during CPR the rescuer pushes on the patient's chest through the extension piece in the vicinity of the electrodes. If the resuscitation control box were to perform analysis during the chest compressions, the chest compressions would be likely to affect the sensed electrical rhythm. Instead, during the pauses between sets of compressions (for example, the pause after every fifth chest compression), the resuscitation control box can perform an electrocardiogram (ECG) analysis. The resuscitation control box might discover, for example, that the patient who is undergoing CPR is experiencing a non-shockable rhythm such as bradycardia, in which case the CPR is required in order to keep the patient alive, but then the resuscitation control box may discover that the rhythm has changed to ventricular fibrillation in the midst of CPR, in which case the resuscitation control box would instruct the rescuer to stop performing CPR so as to allow the resuscitation control box to perform more analysis and possibly apply one or more shocks to the patient. Thus, the invention integrates the rescuer into a sophisticated scheme that allows complex combinations of therapy.

In an alternative embodiment, a compression-sensing element such as an accelerometer may be used in place of a force-sensing element. The accelerometer, such as a solid-state ADXL202 accelerometer, is positioned at the location where the rescuer performs chest compressions. In this embodiment, the microprocessor obtains acceleration readings from the accelerometer at fixed time intervals such as one-millisecond intervals, and the microprocessor integrates the acceleration readings to provide a measurement of chest compression. The use of an accelerometer is based on the discovery that it is more important to measure how deeply the rescuer is compressing the chest than to measure how hard the rescuer is pressing. In fact, every victim's chest will have a different compliance, and it is important that the chest be compressed about an inch and a half to two inches in a normal sized adult regardless of the victim's chest compliance.

Figure 2:
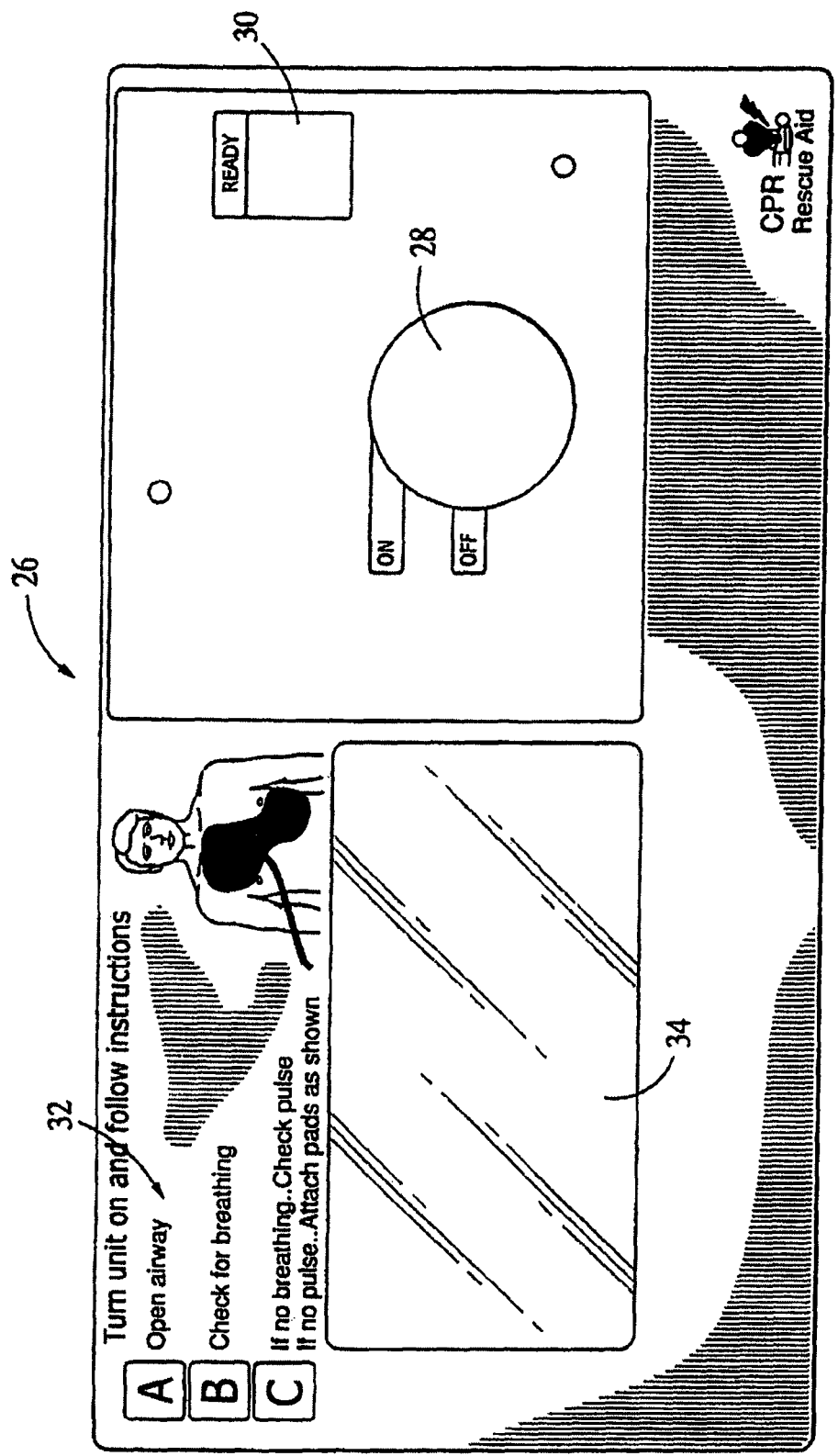
FIG. 2 is a view of the front display panel of a resuscitation control box according to the invention that houses electronic circuitry and provides audible and visual prompting.
Figure 5:
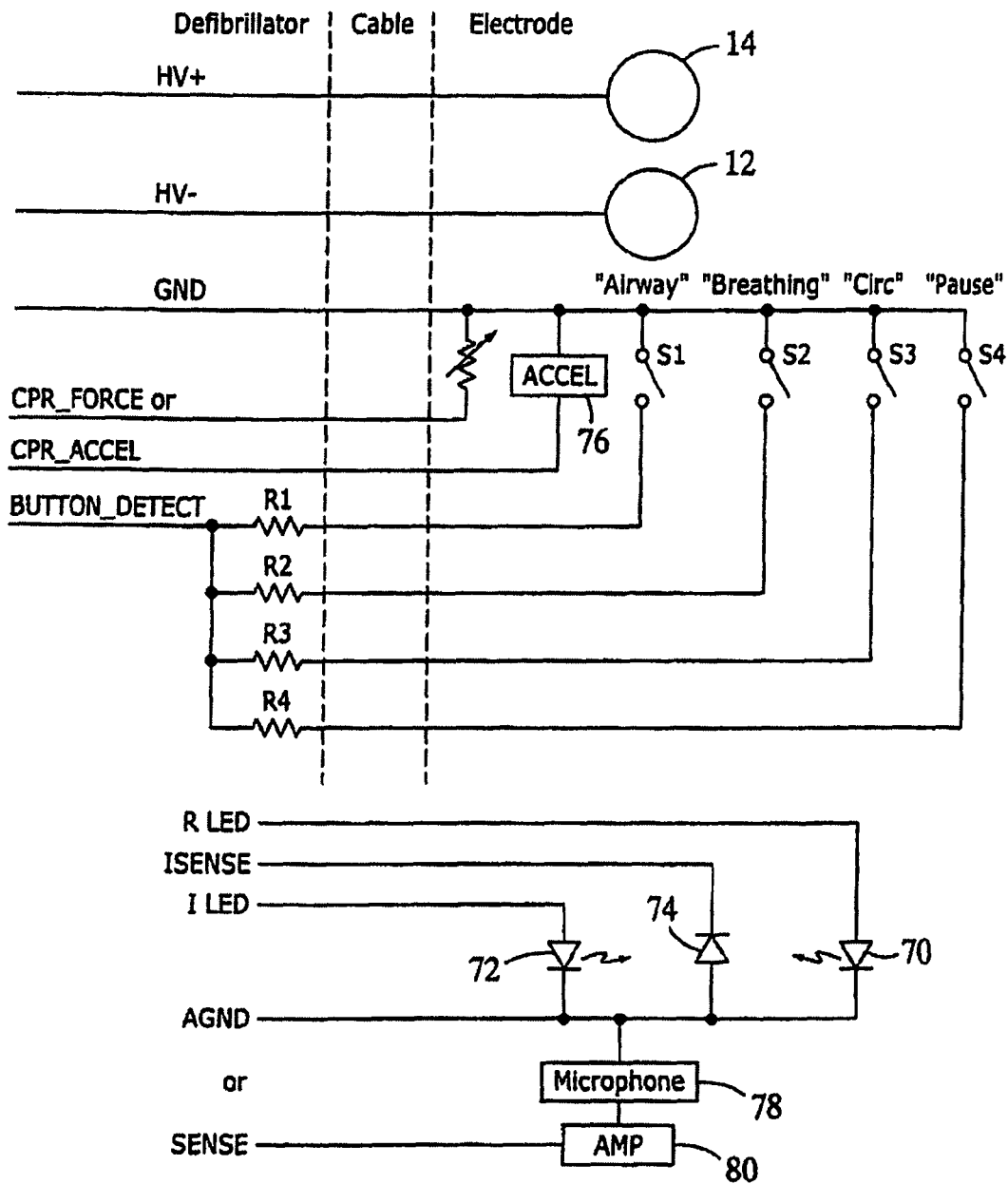
FIG. 5 is a circuit diagram illustrating the circuit interconnections between the defibrillation electrode pad of FIG. 1 and the resuscitation control box of FIG. 2.
Figure 6A:
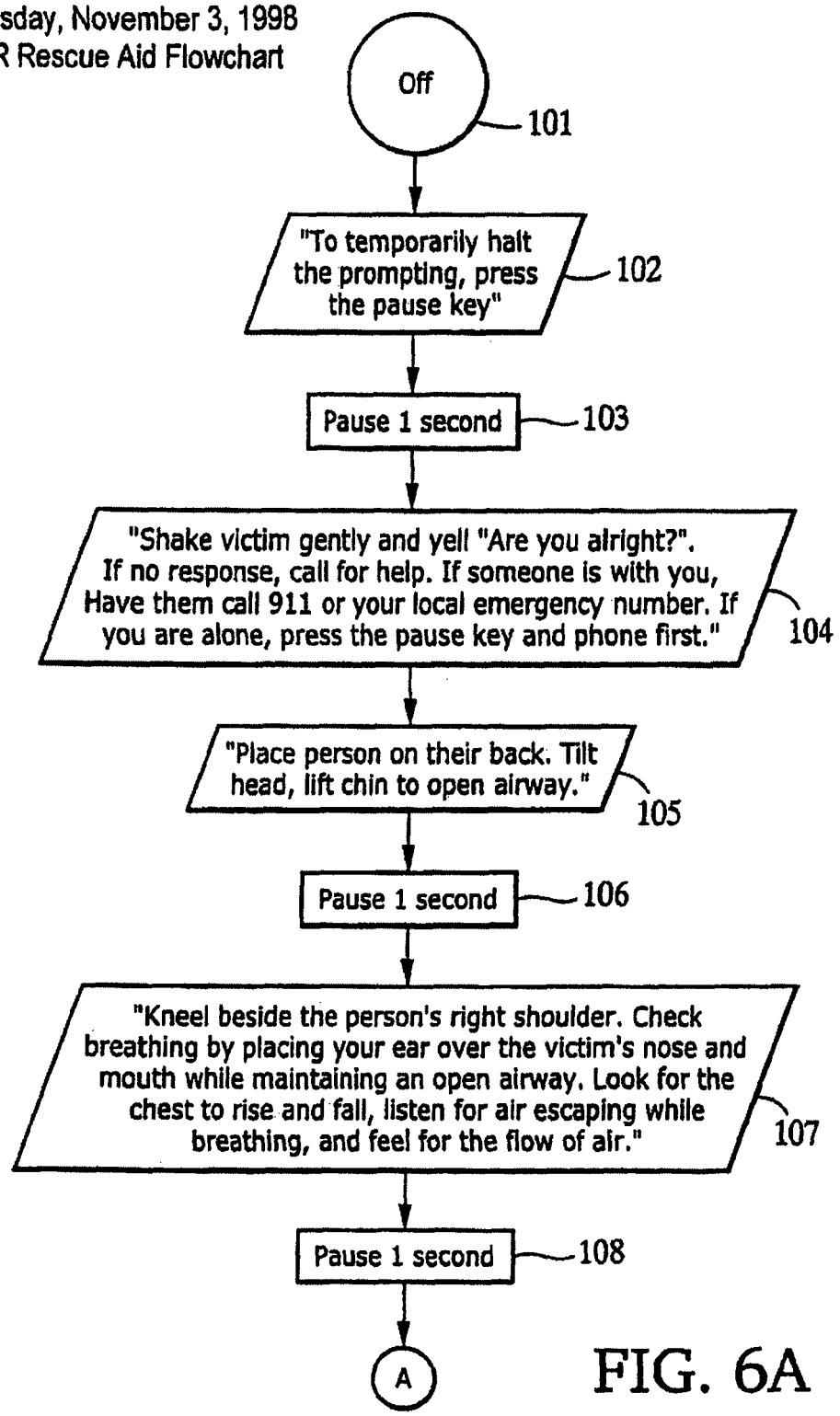
FIGS. 6A and 6B are a flowchart illustrating the initial routine of a resuscitation system according to the invention.
Figure 6B:
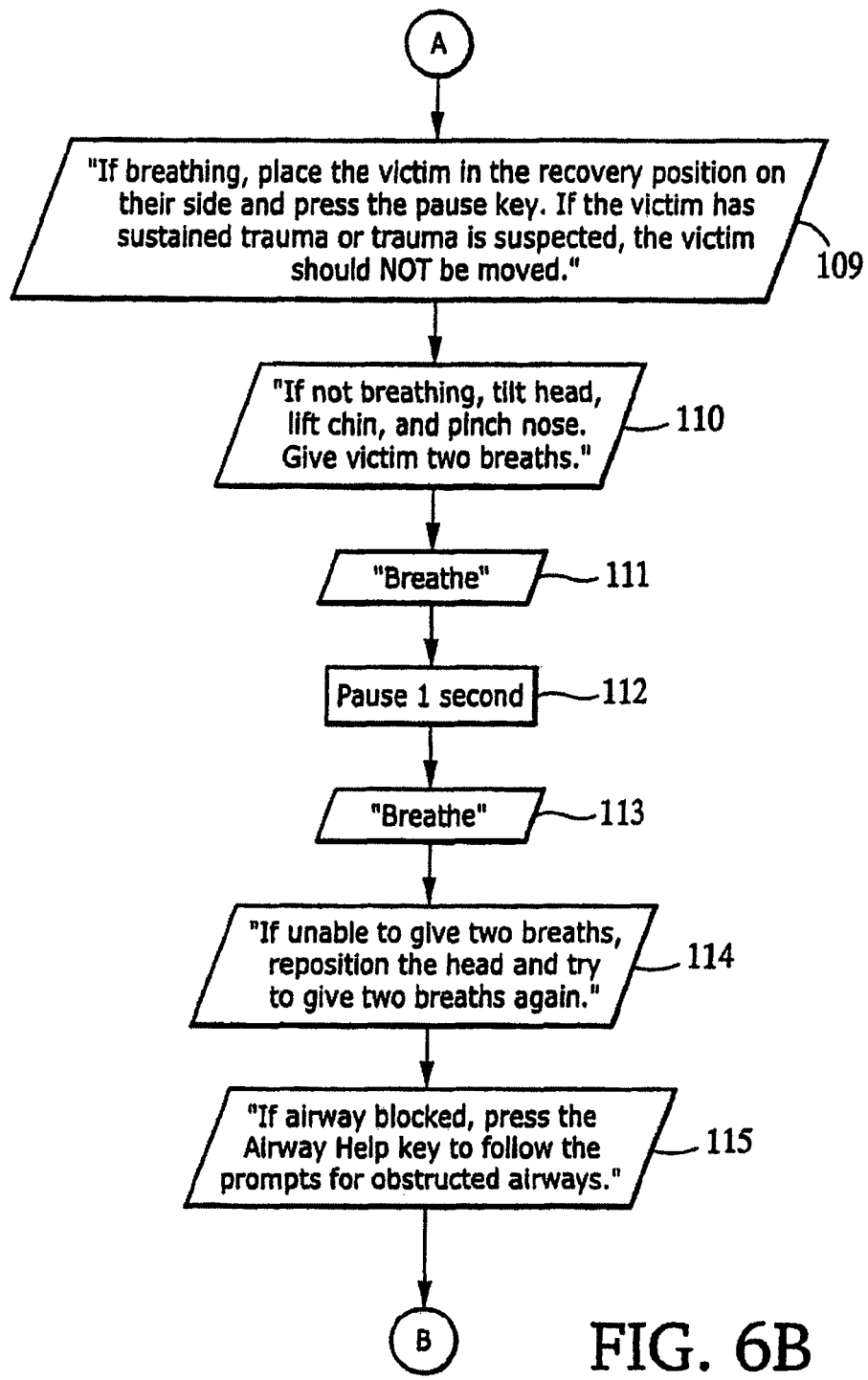

FIG. 5 is a circuit diagram illustrating the circuit interconnections between the defibrillation electrode pad of FIG. 1 through the cable to the resuscitation control box of FIG. 2. Sternum electrode 14 is connected to HV+ at the resuscitation control box, and apex electrode 12 is connected to HV−. A ground GND is connected to the upper conductive ink trace of buttons A, B, C, and PAUSE and to one of the layers of the force-sensing resistor. The other layer of the force-sensing resistor is connected to CPR_FORCE, and the lower conductive ink traces associated with buttons A, B, C, and PAUSE are connected to BUTTON DETECT through resistors R1, R2, R3, and R4. As an alternative to the use of a force-sensing resistor, a compression-sensing accelerometer 76 may be employed, in which case CPR_FORCE is replaced by CPR_ACCEL connected to accelerometer 76. Red light-emitting diode 70, near-infrared light-emitting diode 72, and photodetector diode 74 of the pulse oximetry system are connected to RLED, ILED, and ISENSE respectively, as well as ground AGND. As an alternative to the use of a pulse oximetry system, a phonocardiogram system may be employed, in which case RLED, ILED, and ISENSE is replaced by SENSE connected to microphone 78 and amplifier 80.

FIGS. 6-9 illustrate the routine of the resuscitation system described above, which is based on steps A, B, and C (airway, breathing, and circulation). Because step C includes defibrillation as well as chest compressions, all of the aspects of resuscitation are tied together in one protocol (actually, if defibrillation were considered to be a step D distinct from step C, the sequence of steps would be A, B, D, C).

The first thing the rescuer must do upon arriving at the patient is to determine whether the patient is unconscious and breathing. The rescuer opens the patient's airway, administers breaths to the patient if the patient is not breathing, and checks to determine whether a pulse is present. If there is no pulse, rather than perform chest compressions as in standard CPR, the rescuer allows the resuscitation control box to analyze the patient's electrical rhythm, and if the resuscitation control box determines that the rhythm is shockable, the resuscitation control box causes one or more shocks to be applied to the patient, and then the rescuer performs chest compressions. Thus, the invention provides a first response system that can keep the patient viable until an advanced life support team arrives to perform advanced techniques including pacing, further defibrillation, and drug therapy.

If the resuscitation control box determines that it should apply one or more defibrillation shocks to the patient, it is important that the rescuer not be anywhere near the patient when the shocks are applied to the patient. Prior to application of each shock, the resuscitation control box instructs the rescuer to please press the "ready" button when everybody is clear of the patient. The pressing of the "ready" button verifies that the rescuer's hands are off of the patient.

When the resuscitation control box detects a shockable rhythm, the resuscitation control box provides shocks of appropriate duration and energy (such as a sequence of shocks of increasing energy from 200 Joules to 300 Joules to the highest setting, 360 Joules, with the resuscitation control box performing analysis after each shock to determine whether another shock is required). If the defibrillation therapy is successful, the patient's rhythm is typically converted from ventricular fibrillation, ventricular tachycardia, or ventricular flutter to bradycardia, idio-ventricular rhythm, or asystole, all of which require CPR. It is rare to convert to a normal rhythm. Once the resuscitation control box has caused defibrillation shocks to be applied to the patient, the resuscitation control box automatically senses the patient's condition, and depending on the patient's condition will either prompt the responder to perform CPR or will not prompt the responder to perform CPR.

Defibrillation equipment can be somewhat intimidating to rescuers who are not medical professionals because the equipment can lead the rescuer to feel responsibility for having to save a loved one's life. It is important that the defibrillation equipment reduce this sense of responsibility. In particular, when the rescuer presses the "ready" button, rather than apply a shock immediately that will cause the patient's body to jump dramatically, the resuscitation control box will thank the rescuer and instruct the rescuer to remain clear of the patient and then wait for about two seconds (the resuscitation control box may describe this period to the rescuer as being an internal safety check, even if no substantial safety check is being performed). This process has an effect similar to a conversation that hands responsibility to the resuscitation control box, which makes the decision whether to apply the shock. Thus, the system maintains the rescuer safety features of a semi-automatic external defibrillator, because the rescuer must press the "ready" button before each shock, while appearing to operate more as a fully automatic external defibrillator because the time delay immediately prior to each shock leaves the rescuer with the impression that operation of the equipment is out of the hands of the rescuer. The use of CPR prompts in combination with the defibrillation also adds to the sense that the rescuer is simply following instructions from the resuscitation control box.

With reference to FIGS. 6-9, when the rescuer turns the resuscitation control box on (step 101), the resuscitation control box first informs the rescuer that the rescuer can temporarily halt prompting by pressing the PAUSE button (step 102), and then, after a pause, instructs the rescuer to check responsiveness of patient, and if the patient is non-responsive to call an emergency medical service (EMS) (steps 103, 104). The resuscitation control box then instructs the rescuer to check the patient's airway to determine whether the patient is breathing (steps 105-107).

After a pause, the resuscitation control box then instructs the rescuer that if the patient is breathing the patient should be placed on the patient's side, unless trauma is suspected, and that the rescuer should press the PAUSE button (steps 108-109). Then the resuscitation control box instructs the rescuer to perform mouth-to-mouth resuscitation if the patient is not breathing (steps 110-114). Then the resuscitation control box instructs the rescuer to press an Airway Help button A if the patient's airway is blocked, so that the resuscitation control box can give prompts for clearing obstructed airways (steps 115 of FIG. 6B and 147-158 of FIGS. 9A-9B).

Next, after a pause (step 116a), if the resuscitation control box does not include pulse oximetry or phonocardio gram capability (step 116b), the resuscitation control box instructs the rescuer to check the patient's pulse (step 117). After another pause, the resuscitation control box instructs the rescuer to press a Breathing Help button B if the patient's pulse is okay but the patient is not breathing, so that the resuscitation control box can give prompts for assisting the patient's breathing (steps 118 and 119 of FIG. 7A and 140-146 of FIG. 8). Light-emitting diodes adjacent the various buttons indicate which button has been pressed most recently (only one light remains on at a time). The resuscitation control box next prompts the rescuer to contact an emergency medical system (step 120) and to open the patient's shirt or blouse and attach the adhesive pads (steps 122f-122h).

If the resuscitation control box does include pulse oximetry or phonocardiogram capability (step and 116b), the resuscitation control box prompts the rescuer to open the patient's shirt or blouse and attach the adhesive pads (steps 121 and 122a). If the pulse oximetry or phonocardiogram system does not provide a valid pulsatile reading (step 122b), then the flow chart proceeds to step 117. If the pulse oximetry or phonocardiogram system does provide a valid pulsatile reading and detects a pulse (steps 122b and 122c), then the resuscitation control box begins the breathing help routine (steps 122d of FIG. 7B and step 140 of FIG. 8). If the pulse oximetry or phonocardiogram system does not detect a pulse, then the resuscitation control prompts the rescuer to contact an emergency medical system (step 122c), measures the impedance of the patient to determine whether it is within an acceptable range for application of shocks (step 123) and determines whether the patient's rhythm is shockable (step 124). If the rhythm is shockable, the resuscitation control box causes a sequence of shocks to be applied to the patient, each shock requiring the rescuer first to press the "READY" button on the resuscitation control box (steps 124-131). After the last shock in the sequence, or if the rhythm is non-shockable, the resuscitation control box prompts the rescuer in CPR (steps 132-139). The flowchart then returns to step 117.

FIG. 8 shows the steps 140-146 for prompting the rescuer to assist the patient's breathing. After 12 breaths have been completed (step 144), the pulse oximetry or phonocardiogram system attempts to detect a pulse (step 145a), or, if the system does not include a pulse oximetry or phonocardiogram system, the resuscitation control box prompts the rescuer to check the patient's pulse. If no pulse is present, the resuscitation control box prompts the rescuer to press a Circulation Help button C (step 145b) that brings the rescuer back to the circulation portion of the flowchart. Otherwise, if a pulse is detected, then the flow chart of FIG. 8 returns to step 142.

The combined defibrillation and CPR resuscitation assembly provided by the invention can be less intimidating than conventional AEDs because the assembly is not devoted solely to defibrillation. Moreover, the resuscitation assembly is less intimidating because it accommodates common skill retention problems with respect to necessary techniques ancillary to defibrillation such as mouth-to-mouth resuscitation and CPR, including the appropriate rates of chest compression, the proper location for performing compressions, the proper manner of tilting the patient's head. In addition, because the rescuer knows that it may never even be necessary to apply a defibrillation shock during use of the resuscitation assembly, the rescuer may be more comfortable using the resuscitation assembly for mouth-to-mouth resuscitation and CPR. Unlike previous CPR prompting devices, the rescuer would be required to place the electrode assembly on top of the patient, but the rescuer would do this with the belief that the resuscitation assembly will be sensing the patient's condition and that the likelihood that the resuscitation assembly is actually going to apply a shock is low. If, during this resuscitation process, the resuscitation control box instructs the rescuer to press the "READY" button so that a defibrillation shock can be applied, the rescuer will likely feel comfortable allowing the shock to be applied to the patient. Basically, the resuscitation assembly simply tells the rescuer what to do, and by that point, given that the rescuer is already using the assembly, the rescuer is likely simply to do what the rescuer is told to do. Essentially, the rescuer will be likely to view the resuscitation assembly as simply being a sophisticated CPR prompting device with an additional feature incorporated into it, and since rescuers are less likely to be intimidated by CPR prompting devices than AEDs, they will be likely to use the resuscitation assembly according to the invention when it is needed.

Other embodiments are within the following claims. For example, in other embodiments the system can perform pacing in addition to defibrillation. Pulse detection methods other than pulse oximetry and phonocardiogram may be employed. Any method capable of detecting a victim's pulse can be used with the aspects of the invention calling for pulse detection.

The invention claimed is:

1. An integrated resuscitation system for use by a rescuer to resuscitate a patient, comprising:
    a defibrillation and CPR resuscitation assembly comprising:
        a first high-voltage defibrillation electrode;
        a second high-voltage defibrillation electrode;
        a compression-sensing element mechanically connected with the first and second electrodes, the compression-sensing element comprising an accelerometer and associated circuitry; and
    a resuscitation control unit comprising an internal charge storage capacitor, a microprocessor and associated circuitry configured to be electrically connected to the first and second electrodes and the compression-sensing element and configured to analyze signals generated from the compression-sensing element and at least one of the first electrode and the second electrode and configured to provide resuscitation prompts to the rescuer, wherein at least one of the prompts are based at least in part on use of the compression-sensing element by the rescuer, and wherein the prompts comprise prompting the rescuer to attach the first and second electrodes to the patient, prompting the rescuer to assist a patient's breathing, and prompting the rescuer to apply chest compressions to the patient.

2. The resuscitation system according to claim 1, wherein the assembly is configured to electrically connect with the circuitry of the resuscitation control unit, and wherein the resuscitation control unit is a fully automated external defibrillator.

3. The resuscitation system according to claim 1, wherein the resuscitation prompts further comprise prompting the rescuer to clear a patient's airway.

4. The resuscitation system according to claim 1, wherein the resuscitation prompts further comprise instructions to the rescuer to check the patient's pulse.

5. The resuscitation system according to claim 1, wherein the resuscitation prompts further comprise instructions to the rescuer on placing one of the rescuer's hands on the patient's chest and the compression sensing element.

6. The resuscitation system according to claim 1, wherein the resuscitation prompts based on use of the compression-sensing element are oral prompts.

7. The resuscitation system according to claim 1, wherein the resuscitation prompts based on use of the compression-sensing element are visual prompts.

8. The resuscitation system according to claim 1, wherein the resuscitation prompts based on use of the compression sensing element further comprise prompting the rescuer to apply additional force.

9. The resuscitation system according to claim 1, wherein the resuscitation prompts based on use of the compression sensing element further comprise prompting the rescuer to cease chest compressions if the user is performing CPR at an inappropriate point in time.

10. The resuscitation system according to claim 1, wherein the compression-sensing element comprises a semi-rigid housing.

11. The resuscitation system according to claim 1, wherein the compression-sensing element comprises a housing wherein at least one layer is composed of a rigid material.

12. The resuscitation system according to claim 1, wherein the defibrillation and CPR resuscitation assembly can be disconnected from the resuscitation control unit after use and replaced by another defibrillation and CPR resuscitation assembly.

13. The resuscitation system according to claim 1, wherein the resuscitation control unit analyzes the patient's electrical rhythm to determine if the rhythm is shockable and, if the rhythm is determined to be shockable, automatically causes a shock to be applied to the patient.

14. The resuscitation system according to claim 13, wherein the resuscitation control unit further prompts the rescuer to perform chest compressions.

15. The resuscitation system according to claim 1, wherein the resuscitation control unit is further configured to analyze the patient's electrical rhythm to determine if more than one shock is needed and to increase the energy of a subsequent shock if it is determined based upon the analysis that more than one shock is needed.

16. The resuscitation system according to claim 1, wherein the resuscitation prompts further comprise prompting the rescuer to perform mouth-to-mouth resuscitation.

17. The resuscitation system according to claim 1, wherein the resuscitation prompts further comprise prompting the rescuer to breathe into the patient's mouth.

18. The resuscitation system according to claim 1, wherein the assembly further comprises a pulse detection system.

19. The resuscitation system according to claim 1, wherein the pulse detection system comprises a pulse oximetry system.

20. The resuscitation system according to claim 1, wherein the pulse detection system comprises a phonocardiogram system for listening to the sounds of the patient's heart.

21. The resuscitation system according to claim 1, wherein the resuscitation prompts further comprise prompting the rescuer to check a patient's airway.

22. The resuscitation system according to claim 1, wherein the resuscitation prompts comprise oral and/or visual prompts.

23. The resuscitation system according to claim 1, wherein the resuscitation prompts comprise text prompts.

24. The resuscitation system according to claim 1, wherein the resuscitation prompts comprise oral and text prompts.

25. The resuscitation system according to claim 1, wherein the prompts comprise at least one of prompting the rescuer to contact an emergency medical service, prompting the rescuer to contact an emergency medical system, prompting the rescuer to start CPR, prompting the rescuer to start chest compressions, prompting the rescuer to stop chest compressions, prompting the rescuer to press harder, prompting the rescuer to press faster, prompting the rescuer to press slower, and/or prompting the rescuer to press a button to deliver a shock.

26. The resuscitation system according to claim 1, wherein the integrated resuscitation system comprises at least two of:
    wherein the resuscitation control unit is configured to analyze the patient's electrical rhythm to determine if more than one shock is needed and to increase the energy of a subsequent shock if it is determined based upon the analysis that more than one shock is needed,
wherein the assembly is configured to electrically connect with the circuitry of the resuscitation control unit, and wherein the resuscitation control unit is a fully automated external defibrillator, and/or
wherein the compression-sensing element comprises a semi-rigid housing.

\* \* \* \* \*